United States Patent [19]

Ono

[11] 4,280,500
[45] Jul. 28, 1981

[54] TUBULAR FLEXIBLE MEDICAL INSTRUMENT

[76] Inventor: Kazuaki Ono, 1-8, 5-chome, Koganei-shi, Tokyo, Japan, 186

[21] Appl. No.: 892,121

[22] Filed: Mar. 31, 1978

[51] Int. Cl.³ .............................................. A61M 25/00
[52] U.S. Cl. .............................. 128/348; 128/DIG. 21
[58] Field of Search .................... 128/349 R, DIG. 21, 128/348; 264/288, 345, 346

[56] References Cited

U.S. PATENT DOCUMENTS

| | | | |
|---|---|---|---|
| 3,094,762 | 6/1963 | Jeckel | 128/348 |
| 3,839,240 | 10/1974 | Zimmerman | 264/346 |
| 3,953,566 | 4/1976 | Gore | 264/288 |
| 4,049,589 | 9/1977 | Sakane | 264/345 |
| 4,134,958 | 1/1979 | Dunichey et al. | 264/345 |

FOREIGN PATENT DOCUMENTS

| | | | |
|---|---|---|---|
| 361793 | 10/1922 | Fed. Rep. of Germany | 128/349 R |
| 374641 | 4/1923 | Fed. Rep. of Germany | 128/349 R |

Primary Examiner—Robert W. Michell
Assistant Examiner—Thomas Wallen
Attorney, Agent, or Firm—John S. Campbell

[57] ABSTRACT

A tubular flexible medical instrument of polytetrafluoroethylene capable of easy insertion into and extraction from body cavities. The tube has alternate solid portions and porous fibrillated portions in either a ring or spiral mode. Such a tube has sufficient rigidity to ensure easy penetration of the body cavities and yet the necessary flexibility to permit movement without damage to the cavities and with less pain to the patient.

4 Claims, 8 Drawing Figures

TUBULAR FLEXIBLE MEDICAL INSTRUMENT

BACKGROUND OF THE INVENTION

In many surgical or diagnostic procedures it is necessary that a tubular medical instrument be placed within a body cavity. This instrument accomplishes a variety of purposes including the injection of fluids into the body or the withdrawal of fluids therefrom. Common examples of these types of instruments are catheters and infusion cannula tubes.

Catheter tubes in operation are inserted in the tortuous conduits of the body vessels (e.g., blood vessels) for several deca centimeters. The catheter tubing, therefore, is required to have the appropriate degree of stiffness to insure a smooth insertion combined with the necessary flexibility to allow its advance along the tortuous vessels without impairing the walls. Other important requirements for catheter tubes include dimensional stability, chemical and biological inertness and surface smoothness. These requirements apply equally to blood vessel catheters, urethra catheters and infusion cannula tubes.

Conventional tubular medical instruments for these purposes are made of rather stiff plastics such as polyethylene or nylon. Conventional infusion cannula tubing is about 12 or 13 cm in length and has an outside diameter (O.D.) of about 1.5 mm with an inside diameter (I.D.) of about 0.8 mm. These tubes are fitted at one end with an adapter through which a liquid medicine may be injected into, or a liquid extracted from, the body cavity via the tube. A metal piercing needle is inserted through the tube, the sharp tip of the needle projecting beyond the tube. This needle with the tubing thereon is then thrust through the skin into a blood vessel and both pushed forward until they reach the appropriate position. The needle is then withdrawn, leaving the infusion cannula and attached adapter in position. The adapter is closed with a plug. When an injection of medicine into, or an extraction of blood from the patient is desired, the plug is removed and the adapter is connected to a syringe or suction device.

In order to prevent the infusion cannula tubing from slipping out, the exposed portion must be affixed to the patient by some attaching means, commonly sutures or adhesive tape. In this fixed state, the conventional infusion cannula tubing, being rather rigid, will cause pain and discomfort should the patient move the area of the body in which the tubing is lodged. This problem is particularly acute since the insertion is usually made in a leg, arm, or thigh, thus, greatly restricting the movement of that limb.

SUMMARY OF THE INVENTION

The present invention relates to small diameter polytetrafluoroethylene (PTFE) tubing for use as a catheter. More particularly, this invention relates to PTFE tubing which has solid portions and fibrillated porous portions arranged alternately in a ring or a spiral fashion or any other desirable mode. In this invention, reference to solid PTFE means non-porous PTFE which has a density of about 2.3 g/cm$^3$.

It is an object of this invention to overcome the disadvantages of conventional catheters outlined above and to provide a tubing which causes much less discomfort.

DETAILED DESCRIPTION OF THE INVENTION AND DRAWINGS

Figure 1:
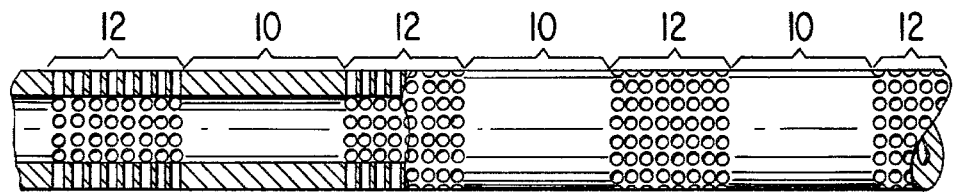
FIGS. 1 through 3 are explanatory drawings of the catheter tubing.

As shown in FIG. 1, the PTFE catheter tube of the present invention is fabricated to have a solid portion 10 and a porous textured portion 12 which are arranged alternately in a ring mode. The lengths of the solid rings 10 and porous rings 12 can be varied according to need. For example, in a catheter tube measuring 2.5 mm O.D. and 1.5 mm I.D., solid portion 10 would be about 5 mm in length and porous fibrillated portion 12 would be about 15 mm in length.

Figure 2:
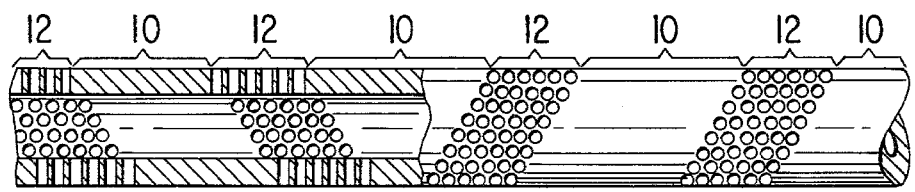

FIG. 2 shows another embodiment of this invention. In this embodiment, solid portion 10 and porous portion 12 alternate in a spiral fashion. The width and pitch of the spiral can be varied according to the required performance.

Figure 3:
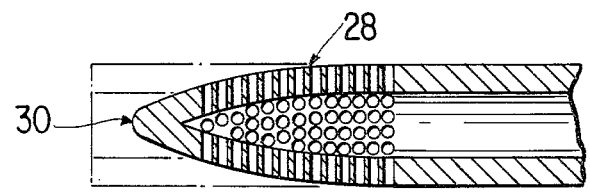

FIG. 3 shows a further embodiment of this invention the top portion 28 (the portion entering the body cavity first) is porous and closed at the end 30. In this manner, gases from the blood or body fluids can be collected without the blood or body fluid penetrating the fine pores into the interior of the tubing.

Figure 4:
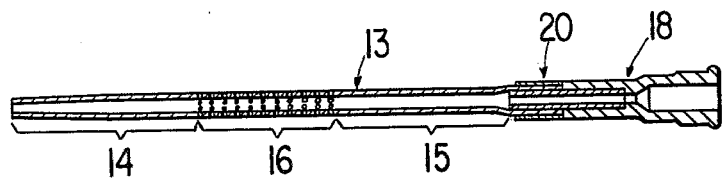
FIGS. 4 through 6 show infusion cannula tubing.

In the embodiment of the invention shown in FIG. 4, the use as an infusion cannula is shown. The tip or top 14 of the tube is solid as is the end 15 which is attached to the adapter 18. These portions 14 and 15 are rather stiff and inflexible. Sandwiched between the two solid portions 14 and 15 is a porous fibrillated portion 16 that is flexible.

To one end of the cannula tubing 13 is fitted an adapter 18 to give a complete infusion cannula. The adapter 18 is connected to the solid portion 15 of the tube 13 by an attaching means herein shown as a metal fastener 20.

Figure 5:
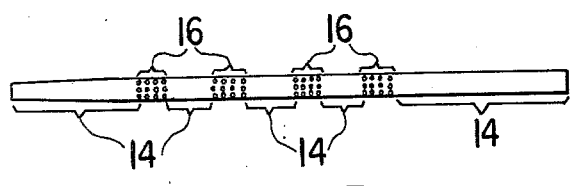
Figure 6:
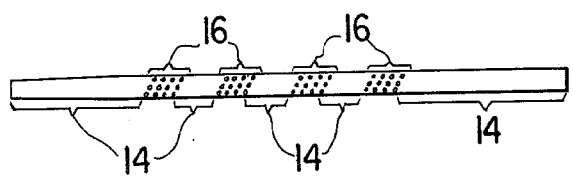
Figure 7:
FIG. 7 shows a needle used for inserting the tube into the body cavity.

FIGS. 5 and 6 show infusion cannula tubing in which there is a series of solid portions 14 and porous fibrillated portions 16 alternating as rings in FIG. 5 and as a spiral in FIG. 6.

The infusion cannula tubing embodiment of the present invention can be used as previously described for conventional cannula tubing.

Figure 8:
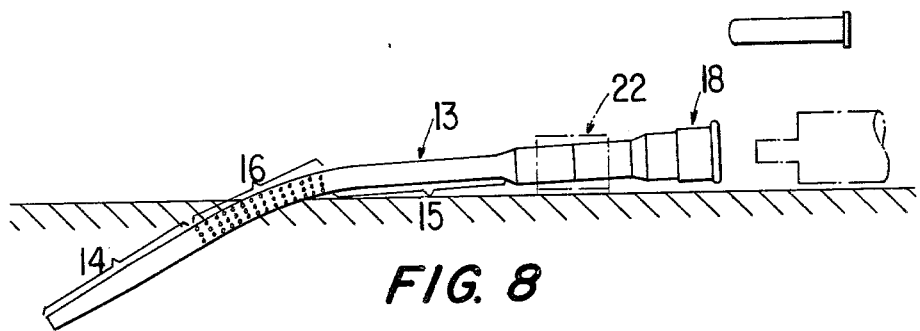
FIG. 8 shows the infusion cannula in position.

FIG. 8 shows tubing 13 in use. A smooth piercing of the skin into the blood vessel is achieved due to the rigidity of the solid portion 14. The middle portion 16 is porous and flexible and, as a result after the tubing 13 is fixed in position by attaching means 22 at portion 15, the tube can bend with less pain and discomfort to the patient permitting a greater mobility of limbs. The tubing, bending at the flexible portion 16, rather than tending to force the embedded tip 14 up against the vessel wall, results in less discomfort and less pain.

The present invention as embodied in the catheter tubing and infusion cannula tubing, described above, has the following advantages:

(1) An appropriate balance of rigidity and flexibility is achieved by alternating along the length of the tube a solid rigid portion and flexible porous portion;

(2) Dimensional stability and/or freedom from kinking under small bend radius due to the presence of the solid portion;

(3) As a result of the tubing being pure PTFE, both the inner and outer surfaces are extremely smooth. This results in easier movement of the tube into, and out of, the body vessels and prevents adherence of foreign matter to either surface;

(4) The excellent heat and chemical resistance of PTFE permit the use of high temperatures and/or strong chemicals for sterilization;

(5) Efficient extraction of blood or body fluid gases can be achieved through the finely porous tip 28 of the embodiment of the invention shown in FIG. 3; and (6) Ejection of a liquid medicine, which has a low surface tension, can be achieved by the embodiment in FIG. 3.

The following examples describe methods of preparing the above described embodiments of the present invention. The stretching step is preferably done according to the teachings of U.S. Pat. No. 3,953,566 herein incorporated by reference. It is, however, anticipated that stretching rates lower than 10% may be used.

The fibrillated porous portion refers to a microstructure comprising a series of nodes interconnected by fibrils. When a porous PTFE structure is raised above its crystalline melt point, unrestrained, it will collapse on itself to form a solid structure. The examples below are meant to illustrate but not limit the scope of the present invention.

EXAMPLE I (1) Following the conventional paste extrusion technique, a PTFE fine powder, available under the Teflon trademark from E. I. DuPont de Nemours, Co., Inc. or the Fluon trademark from Imperial Chemical Industries, Ltd., is mixed with a liquid lubricant such as white oil. The paste is preformed and then ram-extruded through an appropriate die into tubing having the desired diameter and wall thickness depending on the intended use, such as a blood catheter, urethra catheter or infusion cannula tube.

(2) The liquid lubricant may now be removed by appropriate means such as heat evaporation. This step, though preferable, is not essential.

(3) The tubing is then placed on a solid metal rod and insulated intermittently along its length by wrapping with metal foil with space therebetween. The tube on the rod is then placed with its ends unrestrained, in an electrically heated oven or a molten salt bath and raised to a temperature above the crystalline melt point of PTFE, preferably in the range of 360° C. The uninsulated portions will become sintered and shrink lengthwise to form solid portions.

(4) The metal insulating foil is removed, the whole tube still on the metal rod is heated to around 250°–260° C. and expanded to form unsintered porous portions between sintered solid portions.

(5) The resulting tubing is then restrained by clamping the ends on the rod and placed in a constant temperature oven and raised to a temperature above the crystalline melt point of PTFE to produce a catheter tube as shown in FIG. 1.

EXAMPLE II

The material from step 2 of Example I is expanded producing a completely porous tube. This tube is placed on a metal rod and then wrapped with intermittent metal foils with spaces therebetween and heated, unrestrained, above the crystalline melt point of PTFE. The metal foil is removed, the tubing is then restrained as in EXAMPLE I and heated again above the crystalline melt point of PTFE. This is an alternate method of producing the tube shown in FIG. 1.

EXAMPLE III

The porous tube from Example II, after placing on a metal rod, was spirally wrapped with a heat conductive tape and the tape raised, unrestrained, to a temperature above the crystalline melt point of PTFE providing a spirally sintered solid portion. The resulting tube was restrained and heated above the crystalline melt point to produce a tube as shown in FIG. 2 with solid and porous portions in a spiral mode.

In the above examples, the tip portion of the tubes can be rendered porous as described and then the open end closed by suturing or heat sealing. Also, in order that the position of the catheter in the body can be followed, X-ray detectable fillers such as metal powder or BaSO$_4$ may be incorporated at paste formation state.

EXAMPLE IV

The expanded porous tube made according to Example II is cut to a length of about 15–16 cm. The tube is placed on a metal rod, both ends are exposed and the center portion is enclosed in an insulator. The tube is raised, unrestrained, to above the crystalline melt point of PTFE. The end portions shrink back lengthwise to form a solid sintered portion, the middle portion remains porous. The center portion insulator is removed and the tube again raised above the crystalline melt point of PTFE, this time restrained by clamping at the ends to prevent shrinkage. A tube as shown in FIG. 4 is suitable for use as an infusion cannula tubing, after the attachment of adapter, is produced.

EXAMPLE V

The porous center portion of tubing made as in Example IV is placed on a metal rod and wrapped with ring heaters with spaes between adjacent heaters. The heaters are raised above the crystalline melt point of PTFE, the tube being unrestrained lengthwise. Thus, the portions beneath the heaters are sintered and rendered solid by shrinkage. The heaters are then removed, the tube restrained by clamping at the ends, and again raised above the crystalline melt point of PTFE. A tube, as shown in FIG. 5, is thereby produced.

EXAMPLE VI

The porous center portion of tubing made as in Example IV is placed on a metal rod and spirally wrapped with a heating tape and the tape raised to a temperature above the crystalline melt point of PTFE, the tube being unrestrained lengthwise. The heater tape is removed, the tube restrained as before, and again, raised above the crystalline melt point of PTFE. A tube, as shown in FIG. 6, is thereby produced.

While my invention herein has been disclosed, using specific embodiments and examples, these are intended to be illustrative only and not limitative, and changes, modifications or equivalents can be used by those skilled in the art. Such changes within the principles of my invention are intended to be within the scope of the claims below.

I claim:

1. A tubular flexible medical instrument for insertion into a body cavity comprising: a sintered polytetrafluoroethylene tube of solid and porous portions; said solid and porous portions alternating along the length of said tube, said porous portions having a microstructure of nodes interconnected by fibrils.

2. The tubular flexible medical instrument of claim 1 in which said solid and porous portions alternate spirally along the length of said tube.

3. The tubular flexible medical instrument of claim 1 in which said porous portions separate said solid portions.

4. The tubular flexible medical instrument of claim 1 having a porous tip portion.

* * * * *